United States Patent
Falardeau et al.

(10) Patent No.: US 10,405,928 B2
(45) Date of Patent: Sep. 10, 2019

(54) ACETABULUM RIM DIGITIZER DEVICE AND METHOD

(71) Applicant: ORTHOSOFT INC., Montreal (CA)

(72) Inventors: Bruno Falardeau, Verdun (CA); Karine Duval, Montreal (CA); Laurence Moreau-Belanger, Laval (CA); Francois Paradis, Boucherville (CA); Di Li, Lasalle (CA); Myriam Valin, Laval (CA); Benoit Pelletier, Laval (CA)

(73) Assignee: ORTHOSOFT ULC, Montreal (CA)

( * ) Notice: Subject to any disclaimer, the term of this patent is extended or adjusted under 35 U.S.C. 154(b) by 488 days.

(21) Appl. No.: 15/013,518

(22) Filed: Feb. 2, 2016

(65) Prior Publication Data

US 2016/0220315 A1 Aug. 4, 2016

Related U.S. Application Data

(60) Provisional application No. 62/110,872, filed on Feb. 2, 2015.

(51) Int. Cl.
*A61B 34/20* (2016.01)
*A61F 2/46* (2006.01)

(52) U.S. Cl.
CPC ...... *A61B 34/20* (2016.02); *A61B 2034/2048* (2016.02); *A61B 2034/2068* (2016.02); *A61F 2/4609* (2013.01); *A61F 2002/4668* (2013.01)

(58) Field of Classification Search
CPC .............................. A61B 34/20; A61F 2/4609
See application file for complete search history.

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.

(Continued)

*Primary Examiner* — Olivia C Chang
(74) *Attorney, Agent, or Firm* — Norton Rose Fulbright Canada LLP

(57) ABSTRACT

A computer-assisted surgery (CAS) system for tracking an orientation of a pelvis comprises at least one instrument, the instrument having an acetabulum abutment end adapted to be received in an acetabulum, a rim abutment adapted to be abutted against a rim of the acetabulum, and an indicator representative of a physical orientation of the instrument. An inertial sensor unit is connected to the at least one instrument, the inertial sensor unit producing readings representative of its orientation. A computer-assisted surgery processor unit comprises a coordinate system module for setting a pelvic coordinate system from readings of the at least one inertial sensor unit when the at least one instrument has the acetabulum abutment end received in the acetabulum, the coordinate system module setting the pelvic coordinate system by obtaining a plurality of orientation values from the at least one inertial sensor unit when the rim abutment is abutted against locations of the rim, one of said orientation values having the indicator aligned with a reference land- (Continued)

mark, the coordinate system module defining an acetabular plane representative of the pelvic coordinate system from the plurality of orientation values; and a tracking module for tracking an orientation of the at least one inertial sensor unit relative to the pelvic coordinate system during movements thereof using the readings from the inertial sensor unit. An interface outputs orientation data as a function of the pelvic coordinate system.

13 Claims, 5 Drawing Sheets

(56) References Cited

U.S. PATENT DOCUMENTS

| | | | |
|---|---|---|---|
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0021044 A1 | 1/2005 | Stone et al. | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0255584 A1 | 10/2008 | Beverland et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1 | 1/2010 | Park | |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |
| 2010/0082035 A1 | 4/2010 | Keefer | |
| 2010/0087829 A1 | 4/2010 | Metzger et al. | |
| 2010/0152741 A1 | 6/2010 | Park et al. | |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |

(56) References Cited

U.S. PATENT DOCUMENTS

| | | |
|---|---|---|
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0249796 A1 | 9/2010 | Nycz |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0136402 A1 | 5/2012 | Burroughs |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |

(56) References Cited

U.S. PATENT DOCUMENTS

| | | | |
|---|---|---|---|
| 2014/0031722 A1* | 1/2014 | Li | A61F 2/4609 600/587 |
| 2014/0031826 A1 | 1/2014 | Bojarski et al. | |
| 2014/0039631 A1 | 2/2014 | Bojarski et al. | |
| 2014/0052137 A1* | 2/2014 | Gibson | A61B 17/1746 606/91 |
| 2014/0052149 A1 | 2/2014 | van der Walt et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0364858 A1 | 12/2014 | Li et al. | |
| 2017/0296274 A1* | 10/2017 | van der Walt | A61F 2/4657 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |

(56) References Cited

FOREIGN PATENT DOCUMENTS

| | | | |
|---|---|---|---|
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

\* cited by examiner

ACETABULUM RIM DIGITIZER DEVICE AND METHOD

FIELD OF THE APPLICATION

The present application relates to computer-assisted surgery using inertial sensors and more particularly to tools for determining a pelvic tilt for subsequent acetabular cup positioning procedures in hip surgery.

BACKGROUND OF THE ART

In hip arthroplasty, the acetabulum is reamed to subsequently receive therein an acetabular cup. The acetabular cup is an implant that is received in the reamed acetabulum and serves as a receptacle for a femoral head or femoral head implant. Accordingly, tools such as a reamer and a cup impactor are used in the procedure. One of the challenges in such procedures is to provide an adequate orientation to the acetabular cup. Indeed, an inaccurate orientation may result in a loss of movements, improper gait, and/or premature wear of implant components. For example, the acetabular cup is typically positioned in the reamed acetabulum by way of an impactor. The impactor has a stem at an end of which is the acetabular cup. The stem is handled by an operator that impacts the free end so as to drive the acetabular cup into the acetabulum. It is however important that the operator hold the stem of the impactor in a precise three-dimensional orientation relative to the pelvis so as to ensure the adequate orientation of the acetabular cup, in terms of inclination and anteversion.

For this purpose, computer-assisted surgery has been developed in order to help the operator in positioning and orienting the impactor to a desired orientation, notably by enabling the determination of the pelvic tilt, acetabular plane or like orientation data of the pelvis. Among the various tracking technologies used in computer-assisted surgery, optical navigation, C-arm validation and manual reference guides have been used. The optical navigation requires the use of a navigation system, which adds operative time. It also requires pinning a reference on the patient, which adds to the invasiveness of the procedure. It is also bound to line-of-sight constraints which hamper the normal surgical flow. C-arm validation requires the use of bulky equipment and the validation is not cost-effective. Moreover, it does not provide a quantitative assessment of the cup positioning once done, and is generally used post-operatively as opposed to intra-operatively. Finally, manual jigs, such as an A-frame, do not account for the position of the patient on the operative table. Accordingly, inertial sensors are used for their cost-effectiveness and the valuable information they provide.

SUMMARY OF THE APPLICATION

It is therefore an aim of the present invention to provide an acetabulum rim digitizer that addresses issues associated with the prior art.

Therefore, in accordance with a first embodiment of the present disclosure, there is provided a computer-assisted surgery (CAS) system for tracking an orientation of a pelvis comprising: at least one instrument, the instrument having an acetabulum abutment end adapted to be received in an acetabulum, a rim abutment adapted to be abutted against a rim of the acetabulum, and an indicator representative of a physical orientation of the instrument; at least one inertial sensor unit connected to the at least one instrument, the inertial sensor unit producing readings representative of its orientation; a computer-assisted surgery processor unit operating a surgical assistance procedure and comprising a coordinate system module for setting a pelvic coordinate system from readings of the at least one inertial sensor unit when the at least one instrument has the acetabulum abutment end received in the acetabulum, the coordinate system module setting the pelvic coordinate system by obtaining a plurality of orientation values from the at least one inertial sensor unit when the rim abutment is abutted against locations of the rim, one of said orientation values having the indicator aligned with a reference landmark, the coordinate system module defining an acetabular plane representative of the pelvic coordinate system from the plurality of orientation values; and a tracking module for tracking an orientation of the at least one inertial sensor unit relative to the pelvic coordinate system during movements thereof using the readings from the inertial sensor unit, and an interface for outputting orientation data as a function of the pelvic coordinate system.

Further in accordance with the first embodiment, the at least one instrument has a pin guide thereon adapted to position a pin in the acetabulum in a desired location relative to the pelvic coordinate system.

Still further in accordance with the first embodiment, the indicator is a light source emitting a light beam on the reference landmark.

Still further in accordance with the first embodiment, a first of the orientation values obtained has the indicator aligned with a reference landmark.

Still further in accordance with the first embodiment, said first of the orientation values is programmed from preoperative imaging as being representative of a patient orientation.

Still further in accordance with the first embodiment, the tracking module tracks at least one tool supporting one of the inertial sensor unit relative to the pelvic coordinate system.

Still further in accordance with the first embodiment, the tracking module calculates at least one of an anteversion and an inclination of the at least one tool relative to the pelvis.

In accordance with a second embodiment of the present disclosure, there is provided a computer-assisted surgery (CAS) system for tracking an orientation of a pelvis comprising: at least one instrument, the instrument having an acetabulum abutment end adapted to be abutted against a rim of the acetabulum in a planned complementary abutment; at least one inertial sensor unit connected to the at least one instrument, the inertial sensor unit producing readings representative of its orientation; a computer-assisted surgery processor unit operating a surgical assistance procedure and comprising a coordinate system module for setting a pelvic coordinate system from readings of the at least one inertial sensor unit when the at least one instrument has the acetabulum abutment end abutted against a rim of the acetabulum in a planned complementary manner, the coordinate system module setting the pelvic coordinate system by defining an acetabular plane representative of the pelvic coordinate system based on the planned complementary abutment; and a tracking module for tracking an orientation of the at least one inertial sensor unit relative to the pelvic coordinate system during movements thereof using the readings from the inertial sensor unit, and an interface for outputting orientation data as a function of the pelvic coordinate system.

Further in accordance with the second embodiment, the at least one instrument has a pin guide thereon adapted to position a pin in the acetabulum in a desired location relative to the pelvic coordinate system.

Still further in accordance with the second embodiment, the tracking module tracks at least one tool supporting one of the inertial sensor unit relative to the pelvic coordinate system.

Still further in accordance with the second embodiment, the tracking module calculates at least one of an anteversion and an inclination of the at least one tool relative to the pelvis.

Still further in accordance with the second embodiment, the acetabulum abutment end is a tripod having three abutment tabs adapted to be abutted in the planned complementary abutment.

Still further in accordance with the second embodiment, the acetabulum abutment end is patient-specifically fabricated based on preoperative imaging of the patient.

Still further in accordance with the second embodiment, the acetabulum abutment end has adjustable prongs connected to a remainder of the instrument by a lockable joints, for the acetabulum abutment end to be arranged for the planned complementary abutment based on preoperative imaging of the patient.

Still further in accordance with the second embodiment, each said prong has a translational DOF joint and a rotational DOF joint.

In accordance with a third embodiment of the present disclosure, there is provided a method for tracking an orientation of a pelvis in computer-assisted hip surgery comprising: obtaining an instrument having an inertial sensor unit, an acetabulum abutment end adapted to contact a rim of an acetabulum, and a rotation indicator; initializing an orientation of the instrument with the acetabulum abutment end against the rim of the acetabulum and with the rotation indicator aligned with a pelvic landmark; recording the orientation for at least the initial orientation; defining an acetabular plane representative of a pelvic coordinate system from the orientation; and producing orientation data relative to the pelvic coordinate system using inertial sensor units.

Further in accordance with the third embodiment, producing orientation data comprises producing anteversion and/or inclination angles of a tool with an inertial sensor unit relative to the pelvis.

Still further in accordance with the third embodiment, recording the orientation comprises recording a plurality of orientation values each associated with a different contact location between the rim and the acetabulum abutment end.

Still further in accordance with the third embodiment, guiding an installation of a pin whose orientation is known in the pelvic coordinate system.

Still further in accordance with the third embodiment, initializing an orientation of the instrument with the acetabulum abutment end against the rim of the acetabulum and with the rotation indicator aligned with a pelvic landmark is based on preoperative imaging representative of a patient orientation.

DESCRIPTION OF THE EXEMPLARY EMBODIMENTS

Figure 1:
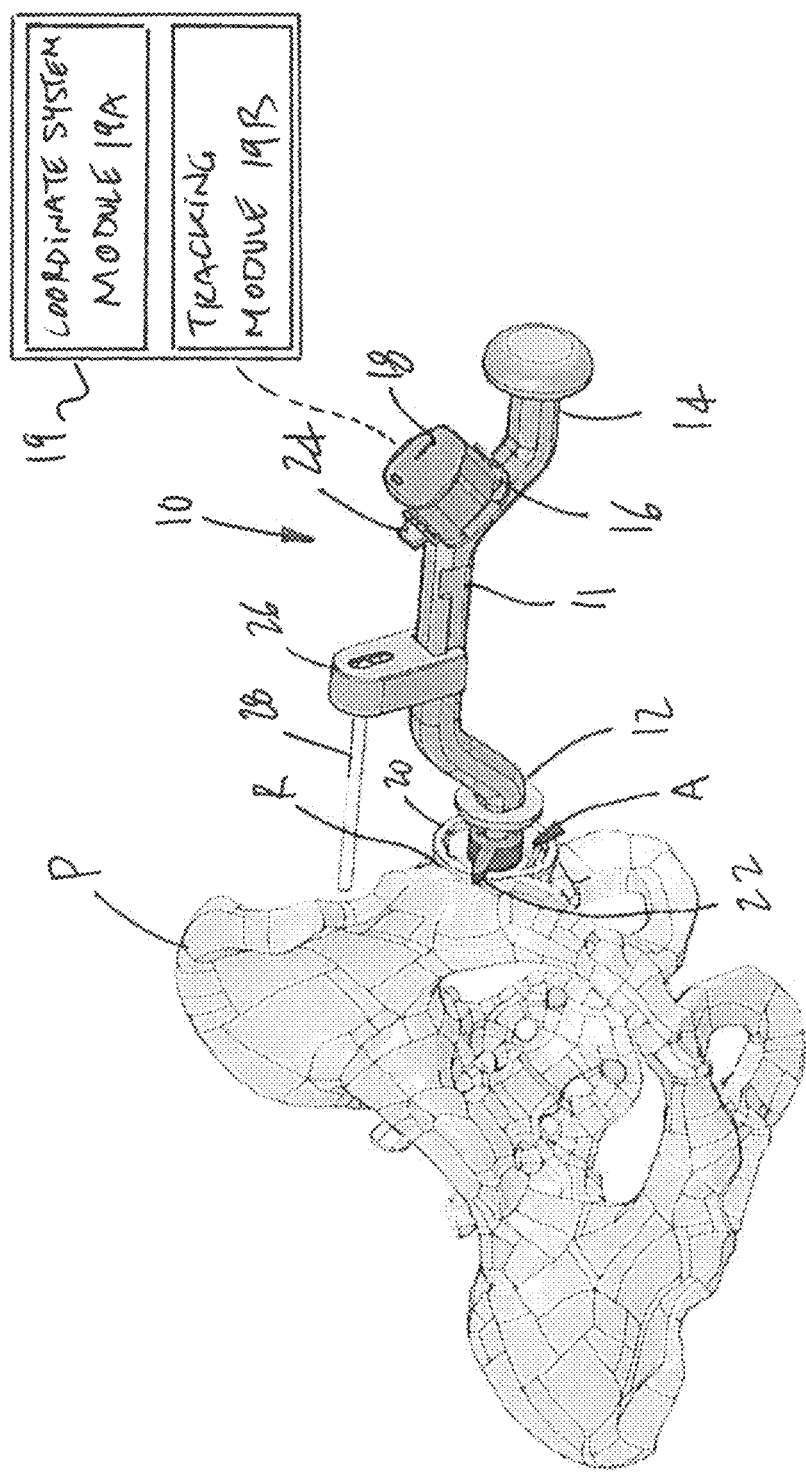
FIG. 1 is a perspective view of an acetabulum rim digitizer device in accordance with the present disclosure, relative to a pelvis.
Figure 2:
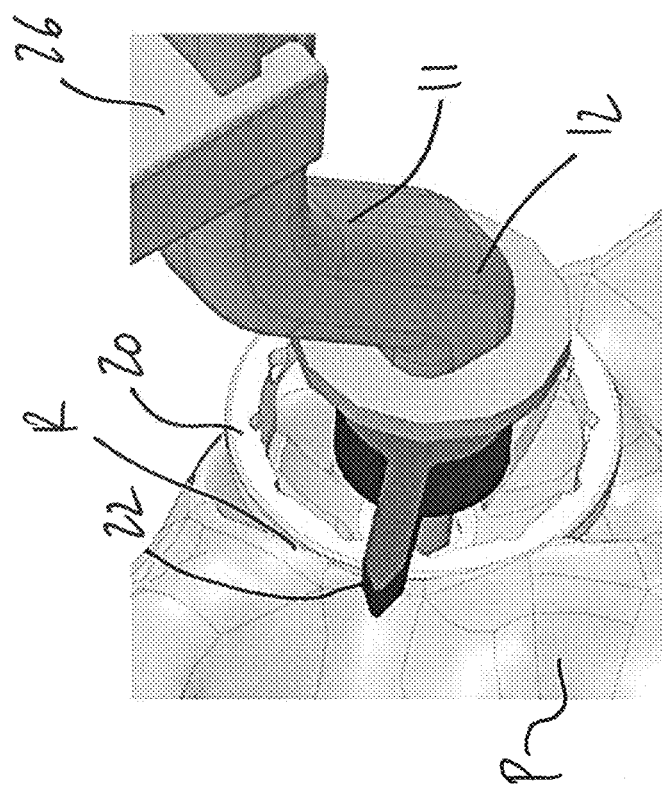
FIG. 2 is an enlarged perspective view of a tooling end of the acetabulum rim digitizer device of FIG. 1.

Referring to the drawings and more particularly to FIGS. 1 and 2, an acetabulum rim digitizer device or instrument is generally shown at 10, relative to a pelvis P having an acetabulum A, the acetabulum having a rim R. The device 10 and method related to the device 10 may be used to determine pelvic orientation data in various forms (e.g., pelvic tilt, anteversion/inclination of acetabulum, etc). The device 10 may also be used to accurately navigate instruments used in hip arthroplasty or like procedures, including bone model and cadaver testing, such as an acetabular reamer, a cup impactor, an impactor guiding pin, using inertial sensors.

The device 10 has an elongated body 11 having a tooling end 12 and a handle end 14. Although illustrated as having an axially offset portion, the body of the device 10 may also be fully straight or have any other appropriate shape.

The device 10 has a receptacle 16 for releasably receiving therein an inertial sensor unit 18, in a known manner. Alternatively, the inertial sensor unit 18 may be integral or embedded into the elongated body 11. The inertial sensor unit 18 may have a gyroscope set to track the orientation of the device 10, by integrating the angular velocity data recorded by the sensor through a registration process. The inertial sensor unit 18 may also comprise an accelerometer set used to calibrate an initial position of the device 10, and to correct gyroscope drift when stable positions are recorded. Other types of inertial sensors may be provided in the inertial sensor unit 18 to complement the data or as alternatives to the accelerometer and/or gyroscope, such as inclinometers, magnetometers, among other possible inertial sensors.

The inertial sensor unit 18 uses its inertial sensor readings to continually calculate the orientation and velocity of a body without the need for an external reference, i.e., no signal transmission from outside of the sensor assembly is necessary, the inertial sensor unit 18 is self-contained. This process is commonly known as dead reckoning and is documented and forms part of the common general knowledge. An initial orientation and velocity must be provided to the inertial sensor unit 18, i.e., the X-Y-Z coordinate system of FIG. 1, after which the orientation is tracked by integrating the angular rates of gyroscope readings at each time step. Wth an accurate estimate of the orientation of the inertial sensor unit 18 with respect to the World frame of reference, gravitational effects can be removed and inertial forces acting on the accelerometers can be integrated to track changes in velocity and position. Since the inertial sensor unit 18 has no need for an external reference, it may be immune to environmental factors such as magnetic fields and operate under a wide range of conditions.

The inertial sensor unit 18 is part of a computer-assisted hip surgery system for navigating instruments, used to implement the method 10, as will be detailed below. The system comprises a computer-assisted surgery (CAS) processing unit 19, that may be a stand-alone computer connected to the inertial sensor unit 18, for instance by wireless communication. It is however pointed out that the CAS processing unit may be partially or entirely integrated into the inertial sensor unit 18, also known as pod. The inertial sensor unit 18, when incorporating the CAS processing unit, may thus be equipped with user interfaces to provide the navigation data, whether it be in the form of LED displays, screens, numerical displays, etc. The computer-assisted surgery (CAS) processing unit 19 may have a coordinate system module 19A and a tracking module 19B, described in further detail hereinafter, and part of a surgical assistance procedure programmed into the CAS processing unit 19.

A hemispherical base 20 is secured to the tooling end 12. The base 20 may be releasably connected to the body 11 (e.g., by screwing engagement) to enable the selection of a base 20 of appropriate dimension, based on the acetabulum being operated on. The geometry of the base 20 may be known as quasi-hemispherical, frusto-spherical, etc. Indeed, as the base 20 is seated into the acetabulum during registration, it is expected that the base 20 is well seated in the acetabulum and does not shift position during the registration process. For this purpose, pressure sensor(s) may be provided on or near the surface of the base 20. The pressure sensor(s) provides signals that can be monitored to determine whether the base 20 is adequately applied against the surface of the acetabulum.

The device 10 may additional comprise a tab 22, which is spaced apart from the base 20 and is designed to be seated on the acetabulum rim for each acquired points, as observed in FIGS. 1 and 2. The device 10 may further have a rotation indicator 24, used to define a fixed rotation axis, not parallel to the rim plane normal, to build a full coordinate system for the acetabulum. In the illustrated embodiment, the rotation indicator 24 is a light source emitting a visible light beam, although other rotation indicators may be used such as a mechanical arm, a laser, a marking on the instrument, or any other visual indicator. A pin guide 26 may also be provided as projecting laterally from the elongated body 11, featuring a slot for guiding the insertion of a pin 28 in the pelvis, following the registration. The rotation indicator 24 is in a known physical orientation in the coordinate system of the inertial sensor unit 18.

The CAS processing unit is programmed with geometric data relating the body 11 (e.g., its axes) to the orientation of the components thereon, such as the base 20, the tab 22 and the rotation indicator 24. This geometric data, obtained pre-operatively, is used by the CAS processing unit (shown as 18) to perform the method and sequence described below.

Still referring to FIG. 1, the acetabulum rim digitizer device 10 may be used intra-operatively with the following intraoperative method:

1. Either prior to or following reaming of the acetabulum A, the base 20 of the device 10 is seated into the acetabulum A. The base 20 has been selected and installed to have a diameter complementary to that of the acetabulum A.

2. The rotation indicator 24 is used to give a predetermined orientation to the device 10. Depending on the embodiment, this rotation indicator 24 may be oriented to point, mark, touch a pre-operatively identifiable landmark. For example, in the case of the pelvis, the identifiable landmark may be lateral anterior-superior iliac spine (ASIS), the 12 o'clock feature of the acetabulum rim, the acetabulum notch, among other features.

3. Registration may be initiated, through the user interface of the CAS processing unit (e.g., button on the inertial sensor unit 18 is turned on).

4. Without unseating the base 20, for example as confirmed from the pressure sensor(s) in the base 20 or by having the operator applying suitable pressure on the device 10, the device 10 is manually rotated to position the tab 22 onto a different segment of the acetabulum rim R (FIG. 2).

5. Either through a user request or through a stability criterion, the inertial sensor unit 18 records the current orientation of the digitizer device 10 and provides feedback to the user, for confirmation.

6. The steps 4-5 are repeated until a sufficient number of acetabulum rim positions are recorded by the inertial sensor unit 18, for instance as indicated by the inertial sensor unit 18 or based on a predetermined number of measurements required.

7. The CAS processing unit (e.g., incorporating the inertial sensor unit 18) then records and provides data related to the acetabulum orientation or pelvic tilt, in any appropriate form (i.e., the pelvic coordinate system).

To perform the method described above, the CAS processing unit must be programmed in the following sequence:

1. The CAS processing unit sets the initial orientation of the acetabulum rim digitizer device 10 when the user initiates the initial recording. This initial position is recorded by assuming arbitrary yaw, roll and pitch are provided by the accelerometer set in the inertial sensor unit 18. From this initial position, and knowing the orientation of the rotation indicator 24 relative to the rim digitizer device 10, the rotation axis may be defined as:

rotation!xtsInWorld

2. After initialization of the registration, the gyroscope set in the inertial sensor unit 18 is used to track the orientation of the acetabulum rim digitizer device 10. The orientation of the device 10 is recorded at the various points of contact between the tab 22 and the acetabulum rim R. The inclination data (roll & pitch) provided by the accelerometer set in the inertial sensor unit 18 may be used to correct drift in the gyroscope data (for instance, using Kalman or Complementary filters). The collection of orientation data at various points provides the orientation of the rim digitizer device 10 in the World coordinate system:

rimDigitizerInWorld

3. At the various points of contact, with the stable orientation the position of the tab 22 may thus be calculated based on the orientation of the rim digitizer device 10 obtained. Each of these positions is recorded in a coordinate system maintained by the CAS processing unit, and is representative of a point on the acetabulum rim R. According to an embodiment, the origin of the coordinate system is located at the center of the hemispherical base 20. As such the position of each point on the rim can be identified as follow:

rimPointInWorld=rimDigitizerInWorld·tabInRimDigitizerCenter

4. When a sufficient number of points has been recorded, the rim points registered can be used to define an acetabular rim plane. According to an embodiment, a plane is fitted through the rim points using an appropriate method such as Least Squares Fitting. This acetabular rim plane is therefore known:

rimPlaneNormalInWorld

5. The acetabular rim plane is used to build an acetabulum coordinate system, as follows:

rimXAxis=rimPioneNormalInWorld rimZAxis=rimTZxis·rotationAxisInWorld rimTAxis=rimZAxis·rimXAxis acetabulumInWorld=[rimXAxis rimYAxis rimZAxis]

6. Using pre-operative planning data (CT-Scan, two-dimensional X-Rays, 3-D modeling, etc . . . ), the pelvis coordinate system is created. Any standard definition may be used, for example the Lewinnek pelvic coordinate system. The pre-operative planning data may be referenced to the acetabulum coordinate system, using the same landmarks and rotation features as used during the registration method. Through data inferred from the pre-operative planning, the relationship between the acetabulum coordinate system and the pelvis coordinate system may be established. By inputting this relationship into the navigation system, the following relationship is obtained:

pelvisInWorld=acetabulumInWorld*pelvisInAcetabulum

7. The gravity axis of the World coordinate system may also be used to determine the pelvic tilt from the computed pelvisInWorld coordinate system.

In the embodiment described above, the acetabular rim plane acquired with landmarks may be matched with a plane defined in pre-operative planning. Alternatively, or additionally, the CAS processing unit may instead match the rim landmarks with a surface defined in pre-operative planning. This surface can be a 3D surface representing the acetabulum rim contour. The CAS processing unit can calculate using Least Squares Fitting the transformation on the acquired rim points which positions the points closest to the pre-planning contour of the acetabulum rim R.

The surface can also be a set of 2D contours, acquired using X-Rays images, combined with respective projective camera calibrations. In one embodiment, camera calibration could be performed as per F. CHERIET et al, Int. J. Patt. Recogn. Artif. Intell. 13, 761 (1999). DOI: 10.1142/S0218001499000434 TOWARDS THE SELF-CALIBRATION OF A MULTIVIEW RADIOGRAPHIC IMAGING SYSTEM FOR THE 3D RECONSTRUCTION OF THE HUMAN SPINE AND RIB CAGE. The CAS processing unit could compute by Least Squares Fitting the transformation on the acquired rim points for which a retro-projection of the points onto the X-Ray, as defined by the projective camera model, is closest to the defined 2D contour.

In another embodiment, an ultrasound device may be fixed to the device 10, for ultrasound readings to be obtained when the device 10 is seated into the acetabulum A. The ultrasound readings may be used to create the rim surface, and thus replaces the tab 22 of the device 10, alleviating the need for physical contact with the acetabulum rim R. As the base 20 is seated into the acetabulum A and the ultrasound device is held still relative to the acetabulum, it is possible to rebuild the acetabulum rim surface accurately in space when combining the ultrasound data with the orientation data provided from the inertial sensor unit 18. This information can be used to match the registered rim contour with the pre-operative planned contour.

Using the device 10, the pin 28 may be positioned to a desired orientation, using the orientation data. For example, the pin 28 may be driven into the pelvis so as to serve as an impactor guide. The longitudinal axis of the pin 28 could thus be driven to an orientation parallel to a normal of the acetabulum rim plane. In an embodiment, the navigation of the device 10 for pin placement is done by providing anteversion and inclination values to the user.

Figure 3:
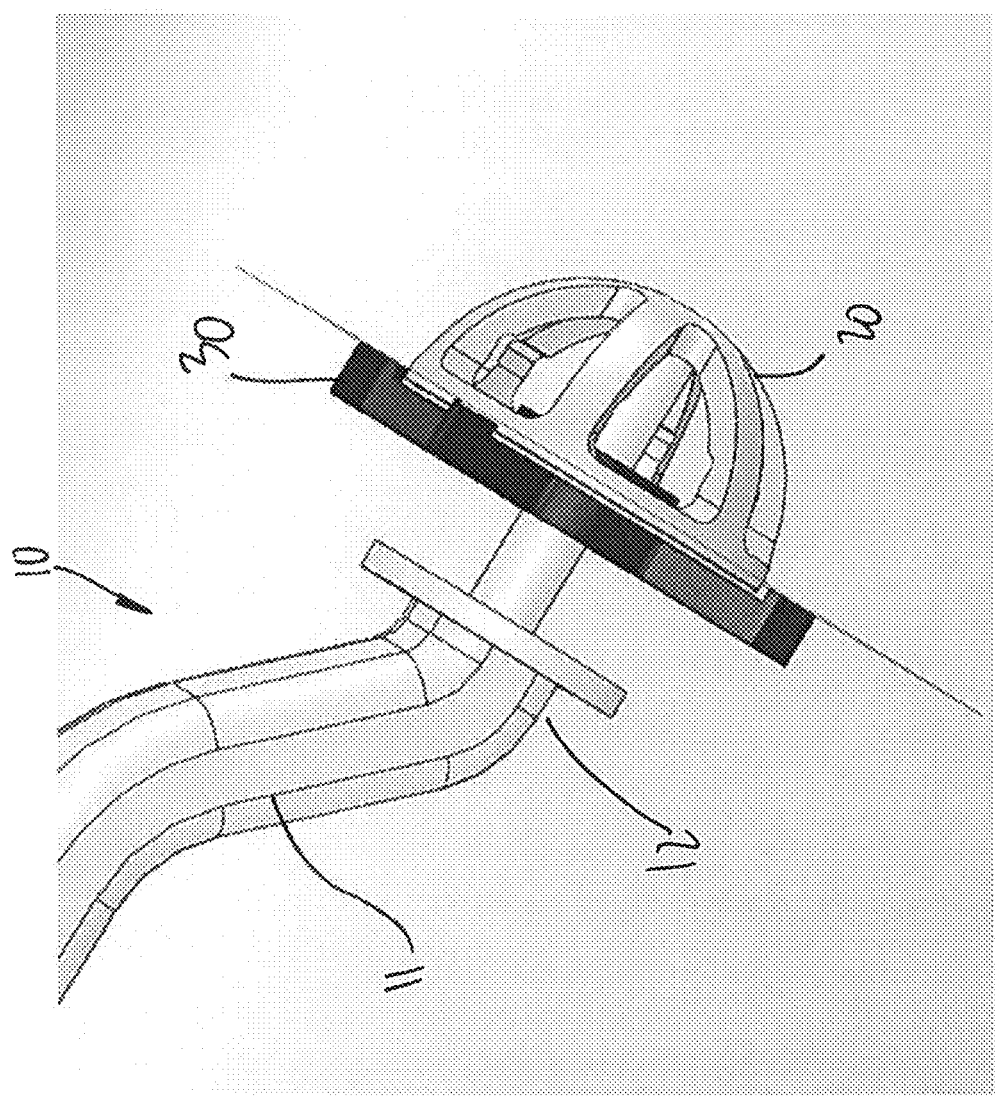
FIG. 3 is an enlarged elevation view of a tooling end of an acetabulum rim digitizer device with planar surface in accordance with another embodiment of the present disclosure.
Figure 4:
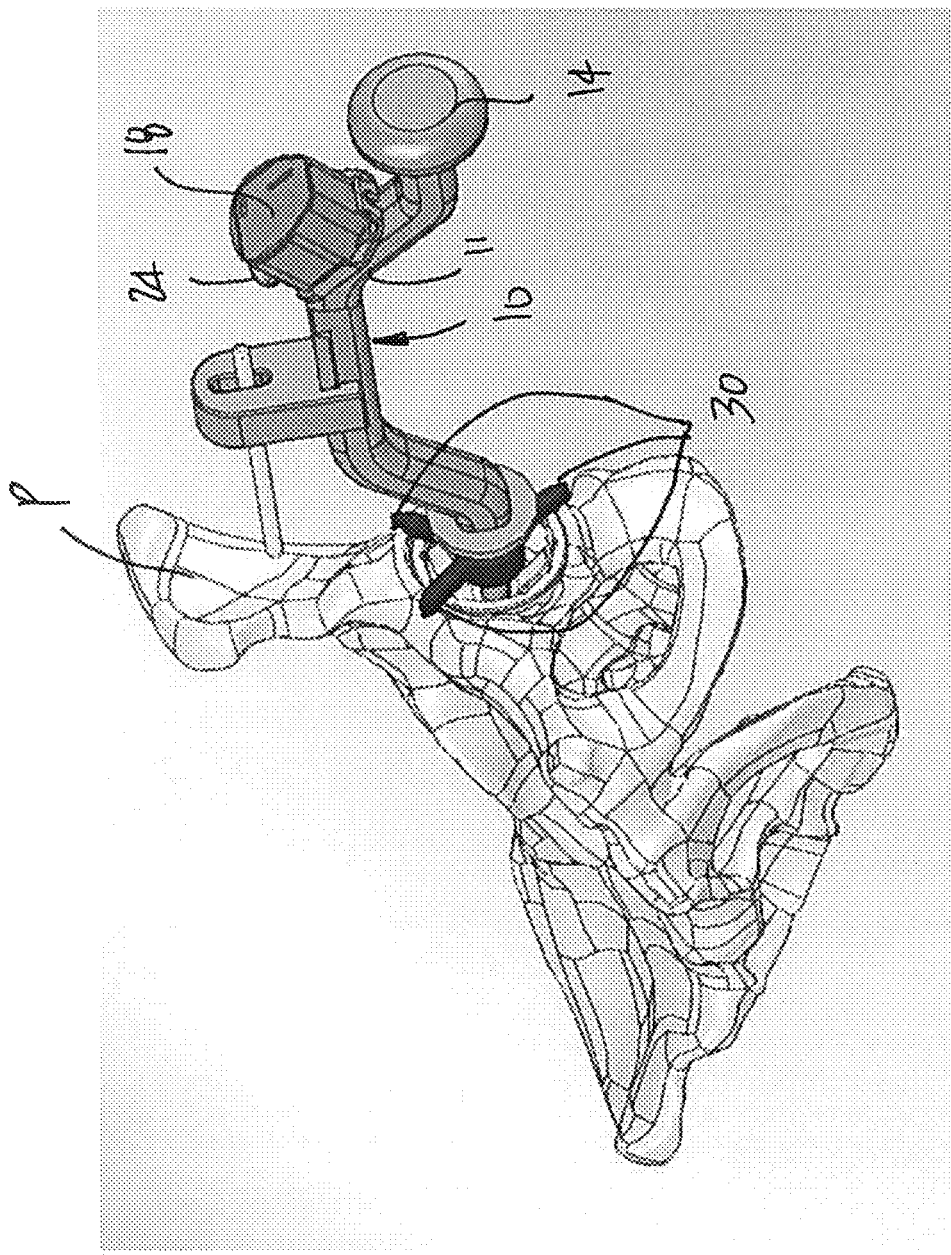
FIG. 4 is a perspective view of the acetabulum rim digitizer device of FIG. 3.

Referring to FIGS. 3 and 4, in yet another embodiment, a planar surface 30, or multiple coplanar features (three fixed tabs in FIG. 4), may be used as an alternative to the tab 22 at the tooling end 12 of the elongated body 11. The base 20 may or may not be present, although the base 20 may provide some manipulation stability to aid in applying the planar surface 30 to the acetabular rim R. The device 10 of FIGS. 3 and 4 could be used to acquire, in a single step, the planar surface as well as the rotation landmark. The device 10 has a configuration that is planned to be in a unique complementary engagement with the rim of the acetabulum, for instance based on pre-operative imaging for instance by having patient specific contact surfaces being negatives of patient tissue for unique complementary engagement. With the embodiment of FIGS. 3 and 4, steps 4-6 of the method described above would not be necessary, provided suitable pre-planning is performed. Similarly, steps 2-4 of the sequence performed by the CAS processing unit are no longer required. The inertial sensor unit 18 may not need a gyroscope set for the embodiment of FIGS. 3 and 4.

Figure 5:
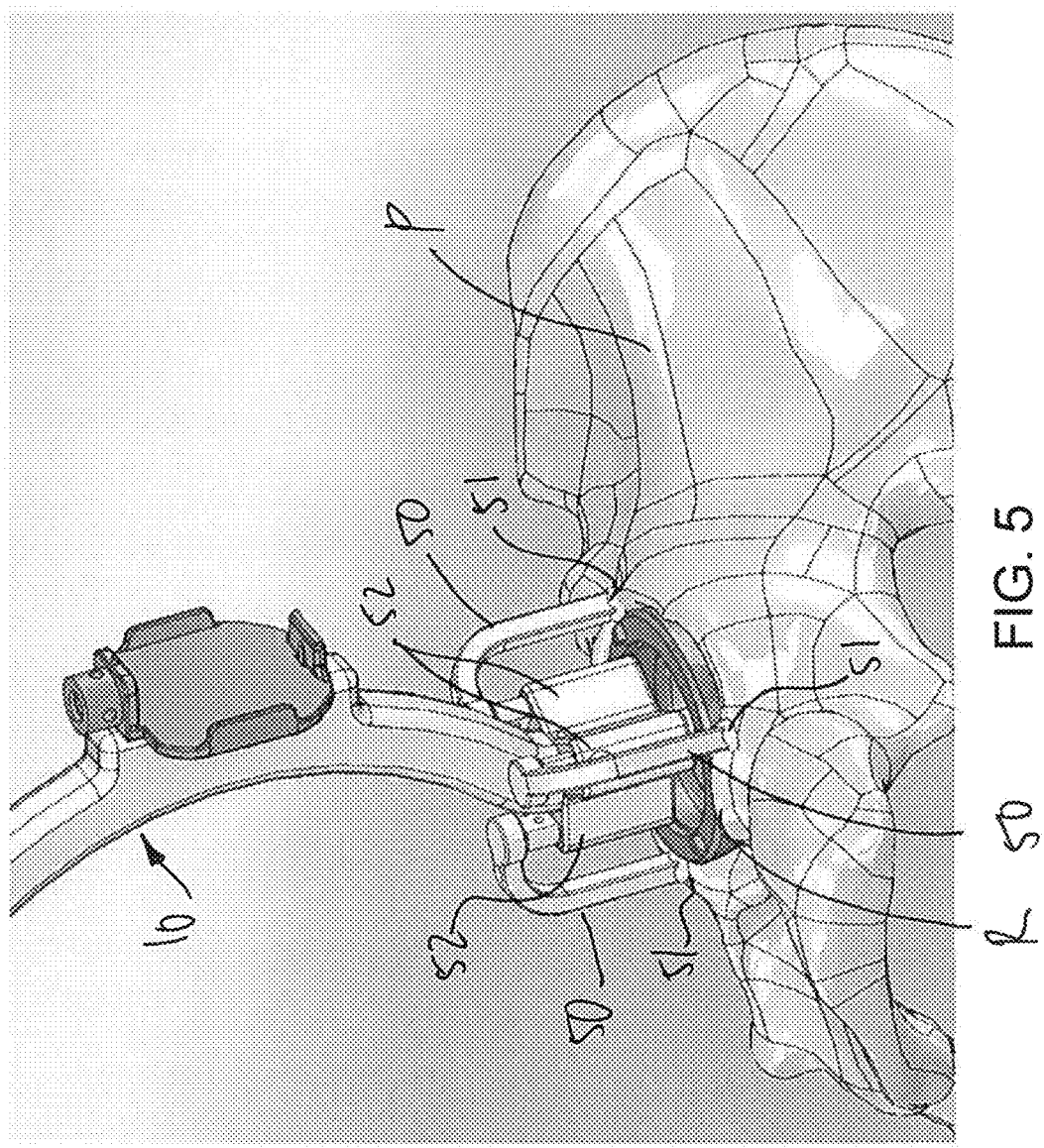
FIG. 5 is a perspective view of an acetabulum rim digitizer device with prongs in accordance with another embodiment of the present disclosure.

Referring to FIG. 5, in yet another embodiment, three adjustable prongs 50 may be used as alternatives to the planar surface 30, effectively forming a tripod. When used, the user is requested to position all of the prongs onto known landmarks (e.g., unique complementary engagement, based on pre-operative imaging). The prongs 50 have abutment ends 51, displaceable axially (e.g., along a longitudinal axis of the body 11) and in rotation (e.g., about an axis parallel to the longitudinal axis of the body 11). Hence, the prongs 50 are each provided with a housing 52 enabling lockable translational DOF and rotational DOF.

The known landmarks against which the ends 51 of the prongs 50 are to be abutted are either defined by identifiable anatomical landmarks, or by for instance, constraining the rotation of the instrument by using a stopper in the acetabulum notch.

For the embodiment of FIG. 5, the pre-operative planning is be used to define the unique adjustments to the tripod to extend to the prongs 50, and to identify the unique position of the device 10 when positioned into the acetabulum A with the predetermined abutment between the prongs 50 and the pelvis P.

As the position of the device 10 of FIG. 5 is unique with regards to the pelvis anatomy, a single reading of an inclinometer in the inertial sensor unit 18 would be sufficient to record the current pelvis tilt.

A method used in combination with the device 10 of FIG. 5 would be as follows:

1 During the pre-operative planning, identify three landmarks to be used.

2. A coordinate system is created from these three landmarks, the relationship between this coordinate system and pelvis coordinate system would also be known from pre-operative planning.

3. From the data computed from the pre-operative planning, the required adjustments on the tripod would be performed to set the position and/or orientation of each prong 50.

4. The device 10 is then positioned in the manner shown in FIG. 5 onto the pre-identified landmarks, either visually or by using a mechanical feature to constrain rotation.

5. When stable, the orientation data for the device 10 is recorded using the inertial sensor unit 18, and this data is used to calculate the pelvis tilt by using the known relationship between the device 10 and the pelvis P.

pelvisInWorld=tripodInWorld·pelvisInTripod

The device 10 of any of the preceding figures is therefore used to provide a means for intra-operatively evaluating the tilt of the pelvis and obtain acetabular orientation data, whether the surgery is performed in supine or lateral decubitus. The data provided by the CAS processing unit may be used, for instance, to reposition the pelvis onto the table, to guide the user in aligning a non-navigated instrument with a desired cup alignment or be used as an input for navigation of surgical instruments during total hip arthroplasty procedure. Although cross-products of axes are discussed above, vectors representative of a direction of the axes may be used for the cross-products.

As shown in FIG. 1, the CAS processor unit 19 may have a coordinate system module 19A and a tracking module 19B. Based on the embodiment the CAS processor unit 19 supports, the modules 19A and 19B may have different functions. For example, for the embodiment of FIGS. 1 and 2, the coordinate system module 19A sets a pelvic coordinate system from readings of the inertial sensor unit 18 when the at least one instrument 10 has the acetabulum abutment end received in the acetabulum. The coordinate system module 19A sets the pelvic coordinate system by obtaining a plurality of orientation values from the inertial sensor unit 18 when the rim abutment tab 22 is abutted against locations of the rim. One of the orientation values has the indicator 24 aligned with a reference landmark. Thus, the coordinate system module 19A defines an acetabular plane representative of the pelvic coordinate system from the plurality of orientation values. The tracking module 19B then tracks an orientation of inertial sensor units relative to the pelvic coordinate system during movements thereof using the readings from the inertial sensor units.

As another example, for the embodiment of FIGS. 3-5, the coordinate system module 19A sets a pelvic coordinate system from readings of the inertial sensor unit 18 when the instrument 10 has the acetabulum abutment end abutted against a rim of the acetabulum in the planned complementary manner. The coordinate system module 19A sets the pelvic coordinate system by defining an acetabular plane representative of the pelvic coordinate system based on the planned complementary abutment. The tracking module 19B then tracks an orientation of inertial sensor units relative to the pelvic coordinate system during movements thereof using the readings from the inertial sensor units.

The invention claimed is:

1. A computer-assisted surgery (CAS) system for tracking an orientation of a pelvis comprising:
   at least one instrument, the instrument having an acetabulum abutment end adapted to be received in an acetabulum, a rim abutment adapted to be abutted against a rim of the acetabulum, and an indicator representative of a physical orientation of the instrument;
   at least one inertial sensor unit connected to the at least one instrument, the inertial sensor unit producing readings representative of its orientation;
   a computer-assisted surgery processor unit operating a surgical assistance procedure and comprising
      a coordinate system module for setting a pelvic coordinate system from readings of the at least one inertial sensor unit when the at least one instrument has the acetabulum abutment end received in the acetabulum, the coordinate system module setting the pelvic coordinate system by obtaining a plurality of orientation values from the at least one inertial sensor unit when the rim abutment is abutted against locations of the rim, one of said orientation values having the indicator aligned with a reference landmark, the coordinate system module defining an acetabular plane representative of the pelvic coordinate system from the plurality of orientation values; and
      a tracking module for tracking an orientation of the at least one inertial sensor unit relative to the pelvic coordinate system during movements thereof using the readings from the inertial sensor unit, and
   an interface for outputting orientation data as a function of the pelvic coordinate system.

2. The CAS system according to claim 1, wherein the at least one instrument has a pin guide thereon adapted to position a pin in the acetabulum in a desired location relative to the pelvic coordinate system.

3. The CAS system according to claim 1, wherein the indicator is a light source emitting a light beam on the reference landmark.

4. The CAS system according to claim 1, wherein a first of the orientation values obtained has the indicator aligned with the reference landmark.

5. The CAS system according to claim 4, wherein said first of the orientation values is programmed from preoperative imaging as being representative of a patient orientation.

6. The CAS system according to claim 1, wherein the tracking module tracks at least one tool supporting one of the at least one inertial sensor unit relative to the pelvic coordinate system.

7. The CAS system according to claim 6, wherein the tracking module calculates at least one of an anteversion and an inclination of the at least one tool relative to the pelvis.

8. A computer-assisted surgery (CAS) system for tracking an orientation of a pelvis comprising:
   at least one instrument, the instrument having an acetabulum abutment end adapted to be abutted against a rim of an acetabulum in a planned complementary abutment, the acetabulum abutment end having a plurality of adjustable prongs connected to a remainder of the instrument by at least one lockable joint;
   at least one inertial sensor unit connected to the at least one instrument, the inertial sensor unit producing readings representative of its orientation;
   a computer-assisted surgery processor unit operating a surgical assistance procedure and comprising
      a coordinate system module for setting a pelvic coordinate system from readings of the at least one inertial sensor unit when the at least one instrument has the acetabulum abutment end abutted against the rim of the acetabulum in the planned complementary manner in which the plurality of adjustable prongs are adjusted so as to be configured to abut the rim in said planned complementary manner, the coordinate system module setting the pelvic coordinate system by defining an acetabular plane representative of the pelvic coordinate system based on the planned complementary abutment; and
      a tracking module for tracking an orientation of the at least one inertial sensor unit relative to the pelvic coordinate system during movements thereof using the readings from the inertial sensor unit, and
   an interface for outputting orientation data as a function of the pelvic coordinate system.

9. The CAS system according to claim 8, wherein the at least one instrument has a pin guide thereon adapted to position a pin in the acetabulum in a desired location relative to the pelvic coordinate system.

10. The CAS system according to claim 8, wherein the tracking module tracks at least one tool supporting one of the inertial sensor unit relative to the pelvic coordinate system.

11. The CAS system according to claim 10, wherein the tracking module calculates at least one of an anteversion and an inclination of the at least one tool relative to the pelvis.

12. The CAS system according to claim 8, wherein each said prong of said plurality has a respective translational DOF joint and a respective rotational DOF joint.

13. The CAS system according to claim 8, wherein the prongs of said plurality are independently movable relative to one another.

\* \* \* \* \*